US007942961B2

(12) United States Patent
Asgary

(10) Patent No.: US 7,942,961 B2
(45) Date of Patent: May 17, 2011

(54) ENDODONTIC FILLING MATERIAL

(76) Inventor: Saeed Asgary, Tehran (IR)

( * ) Notice: Subject to any disclaimer, the term of this patent is extended or adjusted under 35 U.S.C. 154(b) by 839 days.

(21) Appl. No.: 11/778,118

(22) Filed: Jul. 16, 2007

(65) Prior Publication Data
US 2008/0206716 A1 Aug. 28, 2008

(51) Int. Cl.
*A61C 5/00* (2006.01)
*A61C 5/02* (2006.01)
*A61C 5/04* (2006.01)
(52) U.S. Cl. .......... 106/35; 106/690; 106/691; 106/717; 433/224; 433/228.1
(58) Field of Classification Search .................... 106/35, 106/717, 690, 691; 433/224, 228.1
See application file for complete search history.

(56) References Cited

U.S. PATENT DOCUMENTS
7,575,628 B2 * 8/2009 Lu et al. ......................... 106/35
* cited by examiner

*Primary Examiner* — C. Melissa Koslow
(74) *Attorney, Agent, or Firm* — Barry Choobin; Choobin & Choobin Consultancy L.L.C.

(57) ABSTRACT

The present invention is a bioactive endodontic material and its use for filling the tooth and bone cavities. The present invention, by using calcium salt, calcium oxide, calcium silicate, and calcium phosphate compounds as essential constituents, and mixing them with a water base solution, prepares a bioactive calcium and phosphate enriched material. The enriched material (cement) comprises high concentration of water-soluble calcium and phosphate, and immediately forms hydroxyapatite during and after setting. The cement is biocompatible, antibacterial, capable to form an effective seal against reentrance of microorganisms into the filled cavity, compatible to handle and set in an aqueous environment, and able to stimulate hard tissue healing.

16 Claims, 8 Drawing Sheets

ENDODONTIC FILLING MATERIAL

FIELD OF THE INVENTION

The present invention is Sponsored by Iranian National Science Foundation.

The present invention is generally related to a biomaterial particularly medical or dental composition comprising biomineral materials. More particularly, the invention is related to an endodontic material which is suitable for filling and sealing a tooth cavity or root canal system during a dental or endodontic procedure in an orthograde or retrograde manner. Specifically, the invention involves compositions having enhanced adaptation to hydrophilic soft and hard tissues found within oral cavity which assists their ability to effectively fill and seal a newly shaped and cleaned tooth cavity or root canal system, which subsequently formed hydroxyapatite to promote their sealing ability, biocompatibility, antibacterial effect, and also stimulate the repair, regrowth and hard tissue formation.

BACKGROUND OF THE INVENTION

Endodontics or root canal therapy (RCT) IS a part of dentistry sciences that is generally indicated for teeth having sound external structures but diseased, dead or dying dental pulp and/or related tissues. Such teeth mayor may not generally possess intact enamel and dentin and are satisfactorily engaged with surrounding bone tissue. A common aspect of endodontics comprises the treatment of such microorganism infected root canal systems. This procedure involves the dental clinicians' access to the root canal, removal all of the tooth pulp space contents comprising potentially infected and diseased tissues, microorganisms and their by-products from the root canal system of a tooth, disinfecting the root canal using chemo-mechanical techniques, and applying special root canal instruments and irrigation devices to enlarge the root canal space and remove irregularities or rough surfaces within the canal. After that, it is important to fill and seal the evacuated root canal in order to preserve the dead tooth from further reentrance of microorganisms and recurrent decay that might compromise the integrity of the tooth and cause recontamination and infectious disease. Thus the pulp tissue and excised portions of the root should be replaced by endodontic root canal filling materials which are materially safe, stable and biocompatible to living tissues thereby keeping the tooth root safe to periradicular tissues.

The most common root canal filling material is made from "Gutta-Percha" which is a natural resin and a thermoplastic rubber. A basic method involves inserting a preformed filling "cone" or "point" of gutta-percha into a root canal and the cone is laterally or vertically condensed into the canal, so that the point of the cone terminates at the apex of the canal. Remaining many irregularities on the surface and in the shape of canal even after root canal shaping, and the non-adhesive character of gutta-percha had made it impossible to achieve a satisfactory, completely and tridimensionally seal of the root canal system from any leakage of fluids, which may contain microorganisms, in the case of using this material alone.

The filling of the root canal can be further enhanced sealing by inserting sealants, flow able and lubricant materials, along with the gutta-percha points. An ideal root canal sealants should be biocompatible, anti-inflammatory, antibacterial, non-irritating, nontoxic, radiopaque, and have no or minimal shrinkage or even have a slight expansion. They must be preferably unaffected by moisture and to the chemical and physical conditions of the mouth. Ideal prepared sealant, have high wetting and low viscosity, facilitate insertion of filling material into the root canal so that seal the space between filling material and root canal walls. They should also set within a reasonable period of time.

Numerous sealants have been described, such as epoxy, calcium hydroxide and zinc oxide eugenol (ZOE) based sealers. During the root canal filling process, such materials are first applied to the gutta-percha and then inserted into the root canal along with each gutta-percha point or cone. Alternatively, they may be inserted using a file, reamer or lentalo applicator. In this manner, it is hoped that the remaining spaces between the gutta-percha points and the root canal walls can be filled and sealed with the appropriate sealant material. Controlling the exact amount of the sealant or filling material within the border of the root canal to avoid overextension or overfilling has been a challenge for dentists. In the case of overflow of root canal sealant from the apical foramen into the periradicular tissue during a root canal filling process, the excess material should be desirably tolerated by the surrounding tissue while it's better for it to stimulate tissue healing.

One of the drawbacks of using conventional sealants is that such materials tend to be hydrophobic. This makes such materials incompatible with somewhat moist dental hard (which are highly mineralized) and soft tissues within the root canal, which therefore extremely hydrophilic. Thus the hydrophilic nature of the root canal environment inhibits adequate penetrance, complete wetting, and efficient adhesion of the hydrophobic sealant to root canal walls. As a result, a poor seal will be actually observed between the gutta-percha cones and the root canal walls, therefore it may lead to reentrance of mouth microorganisms into the canal and help them to multiply, which subsequently can be finalized as reinfection or other unwished complications. Another point is that the overfilled gutta-percha and conventional sealant materials tend not to have tolerance but also irritate the periapical soft tissues and they do not stimulate healing and hard tissue formation. In addition to all above, these materials are degraded during long-term exposure of tissue fluids that are always present in the mouth.

While there are many techniques for root canal filling, as mentioned, the most widely used technique is the combination of gutta-percha cones and a sealant material. This technique has also been used with root-end fillings (also referred to as retrograde root canal fillings) during periradicular surgery and for the repair of tooth root perforations.

The function of an ideal root-end filling materials is preparing perfect sealing ability in order to interfere with the path of reinfection of microorganism or their byproducts completely, interrupting all paths between root canal system and its external surface. In addition, the root-end filling material should be antibacterial, nontoxic, noncorrosive, nonresorbable, dimensionally stable, easy handling, moisture indifferent, radiopaque, cost-effective, adaptable to the dentinal walls, and finally biocompatible and able to induce regeneration of the bone and periodontal attachment, specifically cementogenesis over the root-end filling itself.

The root-end filling material was used to be the gutta-percha, amalgam, reinforced zinc oxide eugenol cement such as intermediate restorative material (IRM) and super EBA, glass ionomer cement, and mineral trioxide aggregate (MTA). The gutta-percha operation was so difficult, although amalgam has been used for more than a century and has proven itself well tolerated by oral tissues; unfortunately its use is disadvantageous for several reasons: it stains soft and hard tissues, eventually leaks from corrosion, is dimensionally unstable, and moisture sensitive. Reinforced zinc oxide eugenol cements have demerit of releasing eugenol and high-solubility, the IRM weak point is its sensitivity to water, and the super EBA contained mass eugenol and the release of eugenol, high-solubility and inflammatory effect. The glass ionomer cement has sensitivity to water and moisture, the material property is being thick, hard to dense-filling, and its difficult handling. Although MTA has superior biocompatibility in comparison with the conventional root-end filling materials, it has delayed setting time, poor handling characteristics, off-white color, and also a high price.

In case of root perforation(s), the filling material should be able to fill the perforation site effectively and seal the avenue of communication between the oral cavity and the underlying periodontium apparatus. For example, in a multi root tooth, the fork at the junction of the roots forms a "bi or tri-furcation." Thus, perforations in the furcation provide ready access of oral microorganisms to the tissues of the gum. In the case of root perforation the clinician can also apply root-end filling materials as mentioned before, so there is a need for a suitable perforation repair material in the art.

In contrast to endodontic procedures, in other certain dental procedures the pulp of the tooth is left intact. Where the pulp is exposed or partially damaged, a "pulp capping" or "pulpotomy" material is required which will preserve the vitality of the pulp. These materials must also be biocompatible, bioactive, nontoxic, and without any irritation to the pulp. An ideal pulp capping or pulpotomy compounds also allow the regeneration of surrounding tissue and dentine. Calcium hydroxide-based pulp capping or pulpotomy agents are therefore common. The calcium hydroxide technique has a very limited working time before setting. This material is degraded by long-term exposure to tissue fluids that are commonly present in the mouth and also is not impervious to moisture. It is difficult to form a hermetic seal with the calcium hydroxide filling materials. Therefore a need for pulp capping and pulpotomy materials remains which are biocompatible, bioactive, nontoxic, and are capable to stimulate dentin-like tissue formation.

A critical factor in the long-term success of endodontic therapy involves eliminating the leakage around and through a pulp capping or pulpotomy agent, root canal sealant, root canal filling, root-end filling, or the perforation repair material. Intimate adaptation of the filling material to the cavity walls typically plays an important role in elimination of the leakage. However, attaining intimate adaptation is difficult. Therefore, it is desirable to provide compositions and methods which improve the ability of penetrance, wetting, adaptation, filling, and sealing the dental soft and hard tissues surrounding the tooth cavity or root canal system for an endodontic filling material particularly in presence of moisture or water. Having antimicrobial effects and the ability to reduce or eliminate microorganisms, by-products, and their leakage would be an advantage for endodontic filling materials. Biocompatibility, of course, deserves to be mentioned as a high valuable point for these materials. It would be also highly beneficial if the endodontic filling material could be bioactive and stimulus for the repair and regrowth of the potentially surrounding soft and hard tissues so that the dental-like hard tissues will be formed.

Such compositions and methods for more effective filling and sealing of a tooth cavity or root canal system are disclosed and claimed herein.

SUMMARY OF THE INVENTION

The present invention is aimed to provide a novel endodontic filling material capable of overcoming the above-discussed and other drawbacks and deficiencies of the prior art. The present invention discloses an endodontic filling material, comprising: I) a powder, wherein said powder selected from a group consisting of (A) calcium salt compound powder, and (B) calcium oxide compound powder, (Aa) calcium silicate compound powder, and (Ab) calcium phosphate compound powder, wherein ratio of (A) to (B)+(Aa)+(Ab), (B) to (A), (A a) to (A)+(B)+(Ab), or (Ab) to (A)+(B)+(Aa), is between 99 to 111 to 99 percent by weight; II) a liquid, wherein said liquid is selected from a group consisting of: basic, neutralized, acidic water base solution; and III) a mixture, wherein said mixture is prepared by mixing said powder with said water base solution. Said mixture may include other additives typically used in dental materials, treatment of bone defects, filling and sealing tooth cavities and root canals. Such material and method satisfy the existing needs (control of infection, etc.) by providing an antibacterial effect, biocompatibility, stimulation of repair, regrowth and hard tissue formation, and improving the seal against invasive microorganisms and/or their by-products in an aqueous environment.

The use of the novel endodontic filling material provides many advantages over prior endodontic filling and/or sealing materials. This novel filling material is compatible with the hydrophilic environment of mouth. This material provides an acceptable setting in the presence of moisture and blood the moisture of mouth not only adversely affects this material, but also such moisture actually plays an important role in the chemical reactions responsible for better sealing and hardening process. Such character of this material leads to better wetting, penetrance, filling, and sealing, so that more easily manipulation and use in the moisty environment of mouth or bone will be gained. This is particularly important when this material is used for root-end filling where the blood flow is often difficult to control.

Various embodiments of the present invention comprise the novel endodontic filling material and the means for formulating this cement in the way of having easily preparation, transformation, its placement, filling and sealing the tooth cavity or root canal system. This material does not show any shrinkage during its setting, while it has an expansion when it is used in a moist or wet field. Formation of hydroxyapatite in addition to all above can be mentioned as one of the final products of chemical reactions for this material. Therefore a good adaptation with cavity walls, hardening within a desired time, resistance from being washed out, and finally the tooth with an unchanged color will be detected. In the presence of excess material during filling process, it is easy to remove it.

One of significant advantages of the novel endodontic filling material is its good adaptation to dentinal walls and improved sealing ability. Providing a more complete seal of the tooth cavity or root canal greatly increases the ability of resistance from the ingress of liquids into the filled cavity or root canal system. Such liquids, if allowed to enter a cavity or root canal, may introduce microorganisms and their by-products capable of reinfecting the tooth and surrounding bone or tissues. The inventive materials and methods in comparison with the conventional ones improve the ability of sealing the root canal system resulting in yielding a tooth more resistant to microbial leakage. According to common dye penetration method for measuring the effectiveness of root-end filling materials' seal, the novel endodontic filling material of the preferred embodiment of the invention outperforms both IRM (intermediate restorative material, a zinc oxide eugenol base cement) and MTA (mineral trioxide aggregate) cements which are currently used in practice.

The novel endodontic filling material contains antimicrobial agents such as calcium hydroxide and calcium oxide which reduce the microorganisms' existence and neutralized their by-products. In addition, by raising the pH value during the setting process, this material gives an extra antimicrobial effect in sealing areas which may more reduce the possibility of infection or further decay of the tooth structure. It is also sterilized easily.

The novel endodontic filling material utilized in the present invention is bioactive and biocompatible, which favorably allows dental and bone tissues healing. The bioactive particles in the cement composition are characterized by their ability to form hydroxyapatite the principal mineral in teeth and bones and also stimulation and promotion of tissue repair and regrowth in contact to living dental and bone tissues. This is particularly important when it is in direct contact with the exposed or damaged pulp or periapical tissues. The bioactive compositions therefore find particular utility to seal cavities in a wide variety of endodontic treatments which may require a filling or sealing material such as pulp capping and pulpotomy agent, root canal sealant, root canal filling, root-end filling, implant material, bone cement, and as perforation repair compositions.

The present invention includes a method for preparing a novel endodontic filling material which hardens at body temperature and reacts well in contact with tissue fluids. A method of preparation an endodontic filling material, comprising: I) preparing a powder, wherein said powder selected from a group consisting of (A) calcium salt compound powder, and (B) calcium oxide compound powder, (A a) calcium silicate compound powder, and (Ab) calcium phosphate compound powder, wherein ratio of (A) to (B)+(Aa)+(Ab), (B) to (A), (A a) to (A)+(B)+(Ab), or (Ab) to (A)+(B)+(Aa), is between 99 to 1 11 to 99 percent by weight; II) preparing a liquid, wherein said liquid is selected from a group consisting of: basic, neutralized, acidic water base solution; and III) preparing a mixture, wherein said mixture is prepared by mixing said powder with said water base solution. The next steps would be transferring, inserting, and placement of this paste in order to fill and seal the tooth cavity, root canal system, or bone defects before its hardening.

The cement components which is a novel endodontic filling material provides a prefabricate kit which also contains the description for methods of its use.

The above-discussed and other features and advantages of the present invention will be appreciated and understood by those skilled in the art via the following detailed description.

BRIEF DESCRIPTION OF THE DRAWINGS

In order to describe the manner in which features and advantages of the invention are obtained, a more particular description of the invention briefly described above will be rendered by reference to specific embodiments thereof which are illustrated in the appended drawings. Understanding that these drawings show only typical embodiments of the invention and are not therefore considered to limit its scope, the present invention will become clear via the following more detailed description and drawings in which.

DETAILED DESCRIPTION OF THE INVENTION

Figure 1:
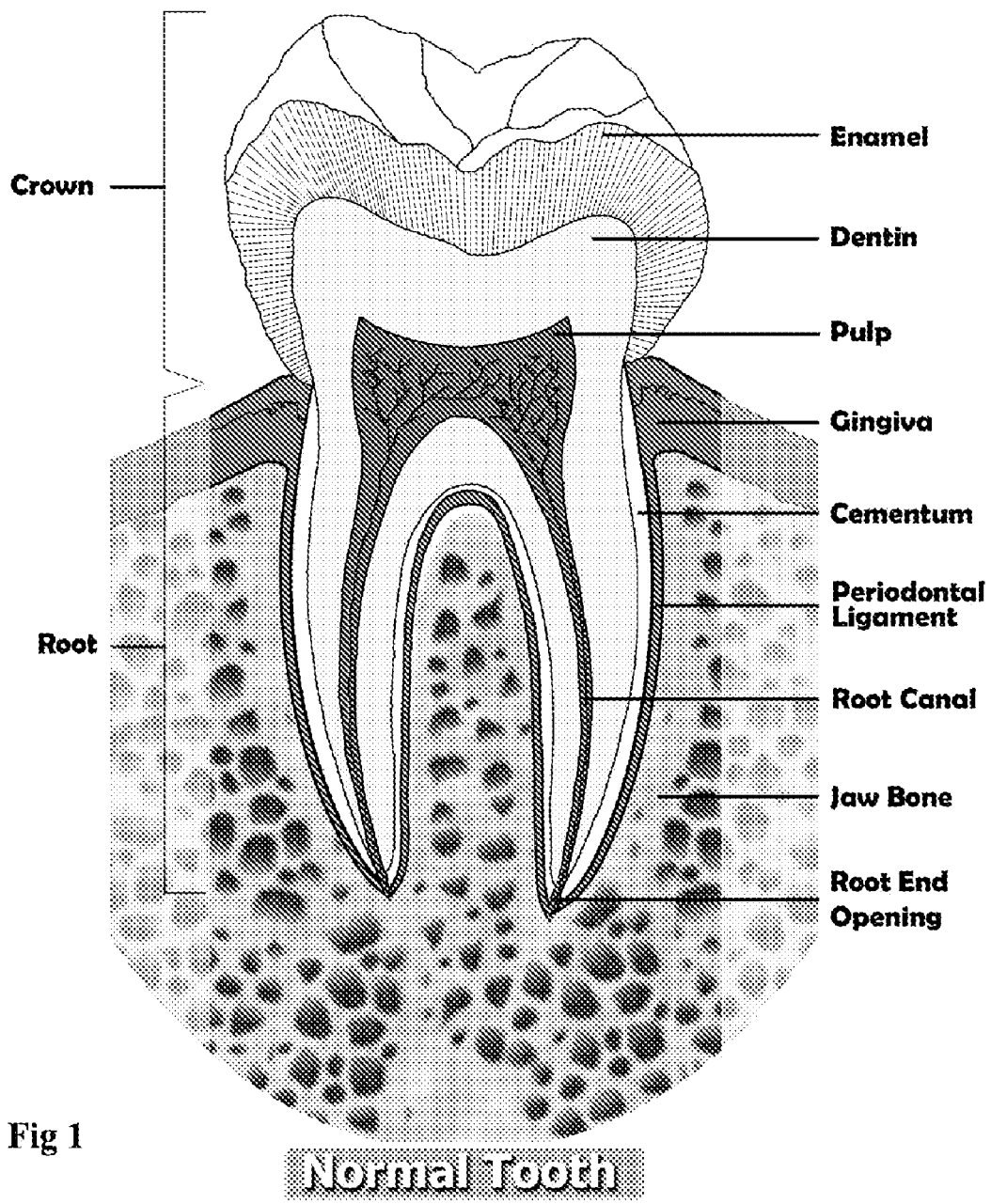
FIG. 1 is a longitudinal view of a healthy mandibular molar tooth showing two roots, a normal pulp and root canals.

As will be appreciated, the present invention provides an endodontic filling material which is a bioactive cement for filling tooth cavity, root canals and bone defect comprising a method of preparation an endodontic filling material, which further comprises: I) preparing a powder, wherein said powder selected from a group consisting of (A) calcium salt compound powder, and (B) calcium oxide compound powder, (Aa) calcium silicate compound powder, and (Ab) calcium phosphate compound powder, wherein ratio of (A) to (B)+(Aa)+(Ab), (B) to (A), (A a) to (A)+(B)+(Ab), or (Ab) to (A)+(B)+(Aa), is between 99 to 1/1 to 99 percent by weight; II) preparing a liquid, wherein said liquid is selected from a group consisting of: basic, neutralized, acidic water base solution; and III) preparing a mixture, wherein said mixture is prepared by mixing said powder with said water base solution; thereby producing hydroxyapatite. The composition may include filler materials, radiopaque materials and other additives selected from a group comprising of: antibacterial agents, bioactive and therapeutic materials, antibiotics, gelling agents, medicaments, osteoinductive factors, anti-inflammatory agents, antioxidants, polymeric resins, pigments, adhesives, cariostatics, crystal adjustors, viscosity modifiers, preservatives, plasticizers, biomaterials, pore forming agents, resorbable and nonresorbable fibers and meshes, and dyes.

Suitable calcium salt, calcium oxide, calcium silicate and calcium phosphate compounds for use as the powder of mixture are biologically active and compatible. It is preferred that the powder is stimulatable by mixing with its solution and/or body tissue fluids. Examples of appropriate calcium salt includes but not limited to calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate. Examples of appropriate calcium oxide include calcium peroxide and calcium hydroxide. Examples of appropriate calcium phosphate includes calcium glycerophosphate, calcium hydroxyapatite or calcium hydroxide phosphate, octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate. Examples of appropriate calcium silicate include tetracalcium silicate, tricalcium silicate, dicalcium silicate, monocalcium silicate, amorphous calcium silicate, or combinations or mixtures of all or some of the above materials.

Preferred calcium salt, calcium oxide, calcium silicate, and calcium phosphate compounds selected from the above list are the tricalcium silicate, dicalcium silicate, tricalcium phosphate, dicalcium phosphate, calcium oxide, calcium hydroxide, calcium sulfate, calcium carbonate, calcium chloride, calcium aluminate, and calcium fluoride. These bioactive minerals can be used to advantage the endodontic filling material in part because of their excellent biocompatibility. In the presence of an aqueous environment, these biominerals produce a large amount of hydroxyl (—OH), calcium (Ca2+), and phosphate (—P04) ions which readily alter and raise the pH of area, form hydroxyapatite (Ca5(P04)30H) crystals (the principal mineral in teeth and bones, as the final product), increase antibacterial activity, stimulate and promote hard tissue formation, and the body tolerates the excess amount. The bioactive material may include any substance or metabolic precursor thereof, which is highly compatible with soft and hard tissues and capable of promoting the growth and survival of cells, tissues, and bone. These bioactive minerals may be present in an amount up to about 99 percent by weight.

A suitable filler as dentin-like or bone growth promoting substance including but are not limited to bioactive glass (typically silicon dioxide containing compositions capable of forming hydroxyapatite in exposure to body tissue fluids), bioactive glassceramic, apatite, hydroxyapatite, bioactive calcium phosphate, Portland cement, bone chip, bone crystal, organic or mineral fraction of bone or teeth, fluoride preparation, silica, fumed silica, amorphous silica, silicate glass, glass fiber, quartz, zinc oxide, gutta-percha, zirconia, biodegradable polymer, bismuth subcarbonate, lithium silicate, tin oxide, alumina, titania, synthetic peptide-containing powder, and the like. The bioactive filler material undergoes chemical reactions at the interface between the soft or hard tissues and the endodontic filling material herein containing the bioactive filler material. The regrowth or repair of destroyed or damaged surrounding tissues will be allowed simultaneously. It is within the scope of the invention to include fillers in an amount of up to about 96 percent by weight of the composition.

The particles of calcium saltloxide/silicate/phosphate compounds may be in the form of a particulate or fibrous in nanosize, microsize, macro size, or mixtures thereof. The characteristics of the cement composition depend upon the size of the particles, by way of example, nanometer-size particles of calcium compounds will promote and accelerate hydroxyapatite formation and cement hardening.

The term "radiopaque" refers to a material that allows the composition to be more easily seen using an X-ray. The radiopaque filler provides the ability to determine how well the endodontic material has penetrated into and filled the tooth cavity, root canal(s) and a bone defect. The radiopacifiers used in endodontic filling compositions include but are not limited to salt or oxide of barium (e.g. barium sulfate), bismuth (e.g. bismuth carbonate, bismuth subcarbonate, or bismuth trioxide), silver (e.g. silver iodide), strontium (e.g. strontium sulfate, or strontium chloride), or titanium (e.g. titanium dioxide); a metal (e.g. tungsten, or tantalum); glass frits containing heavy metal (e.g. barium or bismuths); an organo-iodine compound; or mixtures thereof. The radiopacifiers can be incorporated in composition in the range of up to about 48 (preferably up to about 24) percent by weight.

The inventive endodontic filling material includes antibacterial agent(s) to assist in cleansing and sterilizing the tooth cavity or root canal and to prevent later reinfections. Examples of suitable antibacterial agents are alkaline earth metal oxides (e.g. calcium oxide and calcium peroxide), and alkaline earth metal hydroxides (e.g. calcium hydroxide). A more preferred antibacterial agent is calcium hydroxide. Calcium hydroxide not only kills microorganisms but is also chemically compatible with dental tissues. The antibacterial agent may be included in the composition in a range of up to about 48 percent by weight of the composition.

In many endodontic treatments, the ultimate success of the root canal therapy often depends on the adaptation of the filling material to the tooth walls, and the resultant seal between the material and the remaining tooth structures. An ideal seal will prevent the leakage and migration of microorganisms and other by-products into the cavity. The sufficiency of the seal is particularly important where the pulp chamber or root canal system is to be sealed. The present invention is directed to an endodontic filling material used to fill and seal a cavity or root canal(s) during endodontic treatments. To provide better compatibility with the hydrophilic environment within a tooth or bone, the endodontic sealing or filling material advantageously includes components that are compatible with hydrophilic and mineralized dental tissues. Increased hydrophilic compatibility facilitates wetting of the dental tissues, enables penetration of the filling material within gaps and spaces associated with the root canal(s), and also promotes penetration into the dentinal tubules. Further advantage of this endodontic filling material is that this material in contrast with others not only shows no shrinkage but also demonstrates a slight expansion after its placement in cavity or root canal(s) and setting processes; therefore provides much better adaptation of the endodontic filling material to the tooth walls. The material also forms hydroxyapatite during and after setting or hardening and provides an additional seal at the interface of the material and cavity walls, and the superficial aspect of the filling area the both. Because of these characteristics, the endodontic filling material prevents or significantly reduces microleakage when it is produced and used according to the present invention, therefore enhances the long-term success rate of a wide variety of endodontic treatments which may require a filling and sealing material.

The surface infiltration of the bioactive ingredient of endodontic filling material permits bio-stimulation of the cement before, during and after hardening process, to create unique water-based, calcium and phosphate-containing, biomineral-based composition that facilitates repair and the regrowth of damaged tissues at one interface, while stabilizing the other surfaces and the bulk of cement with respect to sealing properties. Thus, this endodontic filling material becomes a unique optimized one with respect to biocompatibility, bioactivity and sealing ability.

The calcium salt, calcium oxide, calcium silicate, and calcium phosphate compounds include a powder consisting of particles which are hydrophilic and which set in the presence of different kinds of water base solutions. The fact that water is principal for hardening reaction offers a significant advantage over many of other commonly used endodontic filling materials by allowing the cement to set in the wet environment of the body. Generally, the solutions can be divided in numerous groups based on the mechanism by which the solutions accelerate the cement setting reactions and its final properties and products. Mixing the cement with distil or deionize water is the beginning phase of the complex reactions which results a colloidal gel yields a product that self-sets at the ambient or body temperatures to some stable substances such as calcium silicate hydrate and hydroxyapatite. The use of certain calcium and phosphate precursor cement slurry compositions results in a cement which forms the hydroxyapatite in a reliable and quick manner. As mentioned above the resulting hydroxyapatite cement is believed to be biocompatible in contact with hard or soft living tissues. Formation of hydroxyapatite from the calcium salt, calcium oxide, calcium silicate, and calcium phosphate cement slurries can be greatly accelerated by the use of inventive solutions that result in an increase of cationic and anionic components i.e. phosphate, chlorine, and calcium ions concentration and/or increase of the composition's pH, when mixed with cement powder to form a slurry composition. Hydroxyapatite is very low soluble in a wide range of solution pHs, ranging approximately from 4 to 14, while within this pH range, other calcium phosphate compounds have the tendency to dissolve and precipitate as hydroxyapatite. In the pH rang of 10 to 14 hydroxyapatite is at its most stable phase. As the cement powder mix with the water base solution with high pH or phosphate and calcium ions concentration and cement setting reactions proceed the mixture pH increases till the approximate range of 10 to 14, and the more soluble calcium salt, calcium oxide, calcium silicate, and calcium phosphate compounds will begin to dissolve while hydroxyapatite crystals precipitate. The formation of hydroxyapatite and dissolution of the calcium compounds is actually one of the factors responsible for the cement hardening.

In one embodiment the solutions are phosphate buffer saline solution (PBS). PBS is a buffer solution commonly used in biochemistry. It is a salty solution containing sodium chloride, sodium phosphate and potassium phosphate. The solution is isotonic so ions concentration usually matches the human body fluids. This solution has many uses because it is isotonic and nontoxic. After mixing the cement powder with phosphate buffer saline solution, PBS provides an additional source of phosphate ions (—P04) and increase the phosphate concentration in cement slurry so that facilitate and accelerate chemical reactions of —P04 with soluble calcium ions (Ca2+) of the mixture to form hydroxyapatite crystals.

In one embodiment, one or more phosphate and calcium in the water base solutions are generally very reactive with respect to hydroxyappatite crystals' formation, thereby promoting the rate of these crystals' formation and, reducing hardening time of the cement. When the solution is at a higher pH, the phosphate and calcium compounds will be highly soluble in the water. It is hypothesized that the phosphate and calcium compounds act as "seeds" that promote and enhance the hydroxyapatite formation rate. Such circumstances impose the phosphate and calcium compounds' precipitation to form reactive particles that provide a growth template from which hydroxyapatite crystals form.

Another embodiment is salt water based solutions with cationic and anionic components where the anionic components form strong calcium complexes or insoluble salts and free calcium in the solution. Suitable solutions of this type include sodium fluoride, sodium lactate, sodium acetate, calcium chloride, potassium oxalate and the like. When solutions of these types are mixed with a calcium salt, calcium oxide, calcium silicate, and calcium phosphate powder in the case of calcium phosphate components' low level amount the concentration of the free form of the anionic components and the free calcium in the solution is decreased because of their precipitation. Correspondingly, the concentration of phosphate in the solution increases so that the electro neutrality in the solution will be maintained. An increased concentration of phosphate accelerates hydroxyapatite formation and rapid cement setting reactions.

Depending on the type of particular application, various amounts of water base solution may be utilized to form the cement composition. Sufficient amount of the solution is added to the cement to give it a creamy consistency. In using the preferred cement composition as a root-end filling material, the solution content of the mixture is in the range of 20 to 40 (most preferably 25 to 35) weight percent.

For most of the clinical applications, a cement hardening time more than 60 minutes is too long. Additionally, if the cement sets too rapidly, the time of cement manipulation and placement into the tooth cavity, root canal(s), or defect site may not be sufficient. The setting time rate can be adjusted for various final uses, and may be rapid if desired. In accordance with the various embodiments of the present invention, the final endodontic sealing or filling composition will have a hardening time of no more than about 50 (preferably no more than 30) minutes.

The present invention is preferable to the currently available art because, in addition to good enough sealing ability, the compositions of the present invention are expected to be biocompatible, antibacterial, sterilizable, nontoxic, non-mutagenic, noncarcinogenic, radiopaque, impervious to moisture, while it should not provoke any adverse immune response. In various medical and dental treatment procedures, these properties are ideal for regrowth or repair of the surrounding dentine, bone, and soft tissues.

The composition and its methods of use may also be practical for a wide range of potential indications and clinical applications in medicine and dentistry the both. Potential indications include, but are not limited to: an intermediate filling (liner or base), a direct/indirect pulp capping or pulpotomy (vital pulp therapy) agents, a root canal filling or sealing, a root-end filling, a root perforation repair, a bone cement or grafting, and implant materials. The practitioner will realize that there are many suitable applications which fall within the method of the present invention. Examples are shown in FIGS. 1 through 14 and discussed below.

FIG. 1 depicts an example of normal structure of a tooth for which the present inventive material may be used. FIG. 1 shows a longitudinal section of a healthy lower molar tooth with crown and roots, enamel, dentine, cementum, periodontal ligament, alveolar bone, pulp tissue, and the root canals. In a living tooth, the pulp cavity and root canals are filled with fine connective tissue which contains blood vessels, nerves, and specific cells. Dentin is the peripheral dress of the pulp and is continuously formed by odontoblast cells throughout the life. The dentin of crown and root areas is covered by a layer of enamel and cementum respectively.

Figure 2:
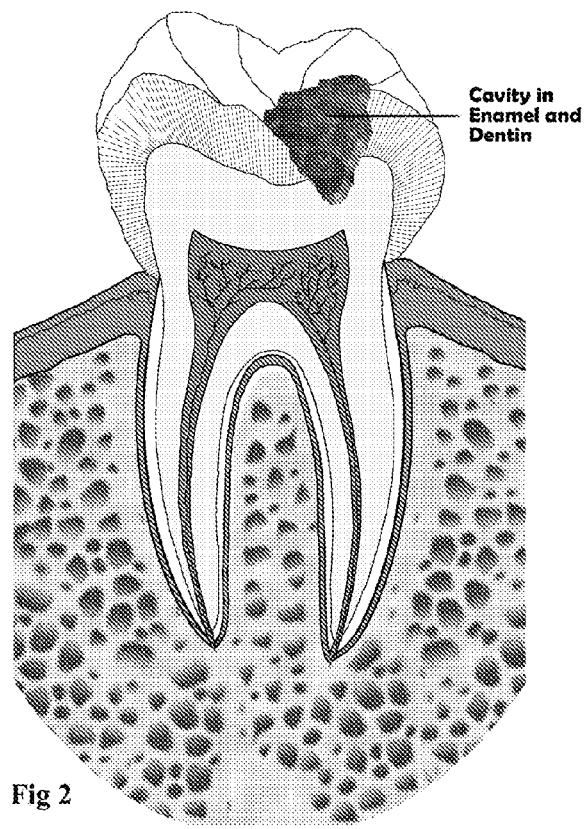
FIG. 2 is a longitudinal view of the tooth of FIG. 1 III which decay has penetrated through the enamel and dentin.
Figure 3:
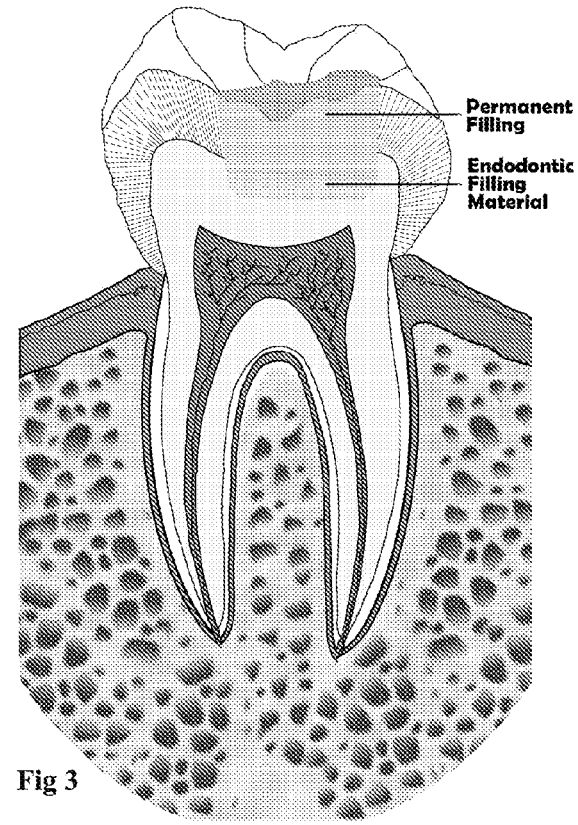
FIG. 3 is a longitudinal view of the same tooth in FIG. 2 in which decay has been removed and the endodontic filling material has been used as an indirect pulp capping agent or an intermediate filling (base) for a permanent filling material.

FIG. 2 shows a longitudinal view of a tooth in which the tooth is damaged and decay has penetrated through the enamel and dentin. Such a tooth needs to be treated with a simple method as follow: a) the cavity identified and prepared, b) the inventive endodontic filling material mixed, transferred, inserted, filled and sealed the base of the prepared cavity as an indirect pulp capping or intermediate filling material (base), and c) the remaining part of the cavity is filled with another permanent filling material (FIG. 3).

Figure 4:
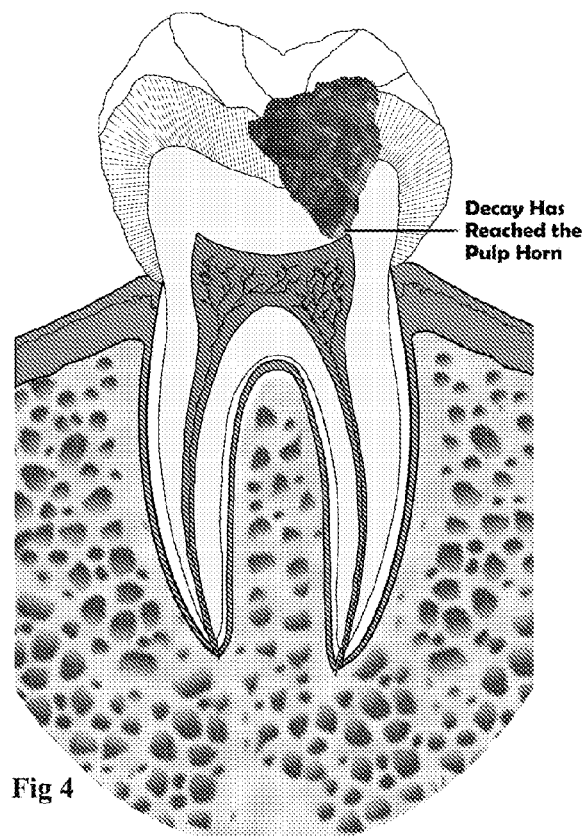
FIG. 4 is a longitudinal view of the tooth of FIG. 1 in which decay has reached the pulp.
Figure 5:
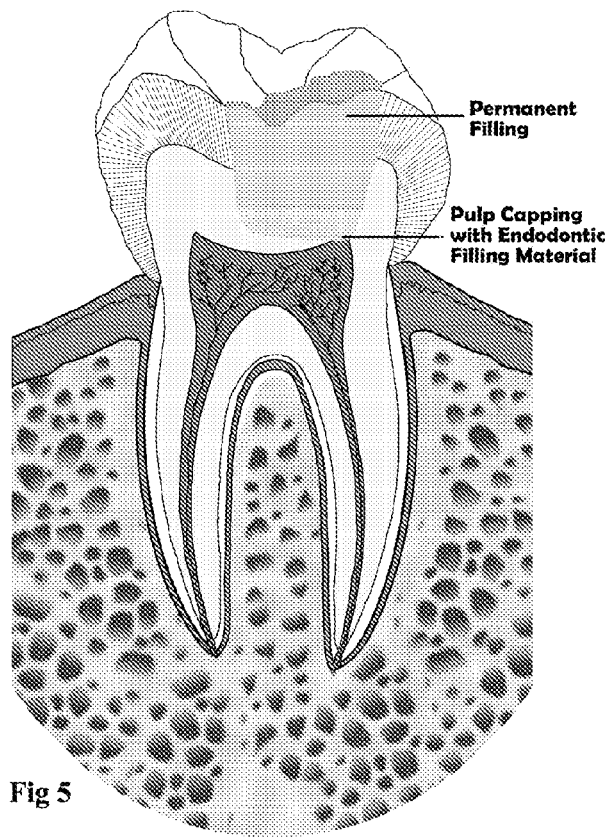
FIG. 5 demonstrate a longitudinal view of the tooth of FIG. 4 in which decay has been removed, the endodontic filling material has been used as a direct pulp capping agent, and a permanent filling has been inserted.

The vital pulp therapy application methods (direct pulp capping or pulpotomy) can be accomplished in a simple procedure. When an exposure of the pulp occurs, the powder and liquid are mixed to form a vital pulp therapy agent just before the use, and this compound will be inserted into the exposure site. FIG. 4 depicts a longitudinal view of a damaged tooth in which decay has penetrated through the enamel and dentin, and probably reached the pulp horn. Such a tooth needs to be treated with a simple method as follows: a) the decay has to be removed, and in the case of the pulp exposure during cavity preparation b) the pulp bleeding is controlled, c) the inventive endodontic filling material is mixed, transferred, inserted, and cap the pulp exposure, fill and seal the base of the prepared cavity, and finally d) the remaining parts of the cavity are filled with the permanent filling material (FIG. 5). A surprising finding of this procedure, during direct pulp capping, was a high degree of pulpal vitality and dentinal bridge formation when the inventive endodontic filling material was utilized by its particular method of use.

Figure 6:
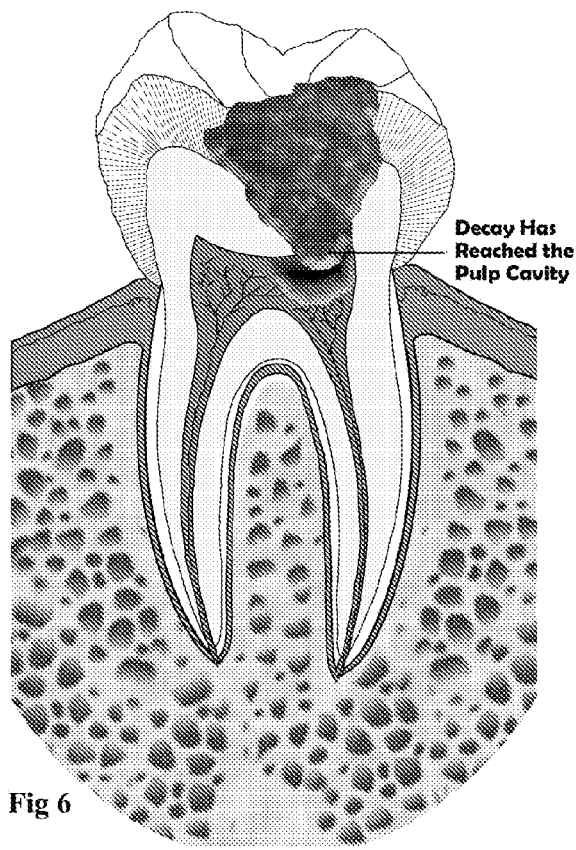
FIG. 6 is a longitudinal view of the tooth shown in FIG. 1 in which decay has reached and damaged the coronal pulp partially.
Figure 7:
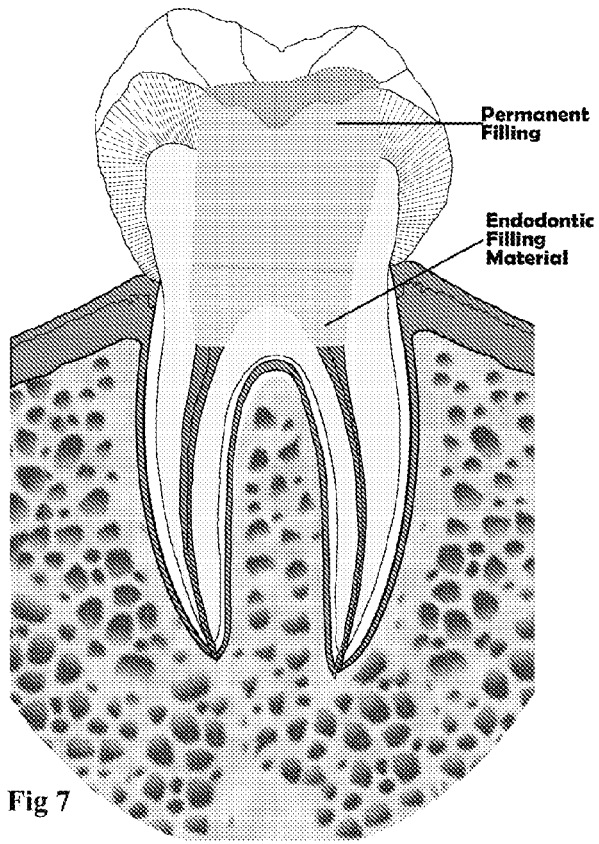
FIG. 7 is a longitudinal view of the tooth of FIG. 6 in which decay has been removed, pulpotomy procedure has been done and the endodontic filling material has been used as a pulpotomy agent, and a permanent filling has been inserted.

FIG. 6 shows a longitudinal view of a damaged tooth. The decay has penetrated through the enamel and dentin, reached the pulp, and partially damaged the coronal pulp. Such a tooth needs to be treated with a method as follows: a) the decay has been eliminated and the pulp tissue is exposed, b) the entire coronal pulp is removed, c) the radicular pulp bleeding has been controlled, d) the inventive endodontic filling material is mixed, transferred, inserted, and it filled and sealed the pulp chamber, and d) the remaining parts of the cavity are filled with the permanent filling material (FIG. 7).

Figure 8:
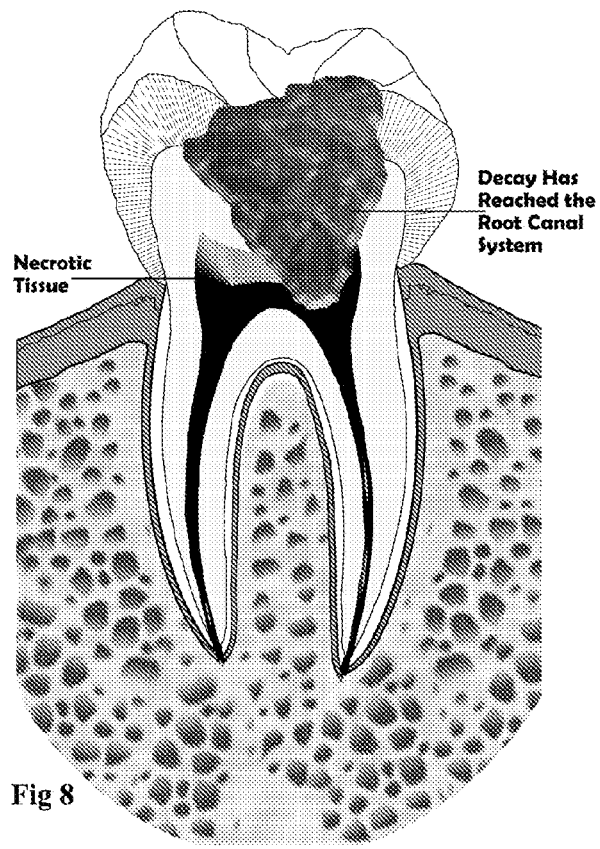
FIG. 8 is a longitudinal view of the tooth of FIG. 1 in which decay has reached and thoroughly damaged the pulp.
Figure 9:
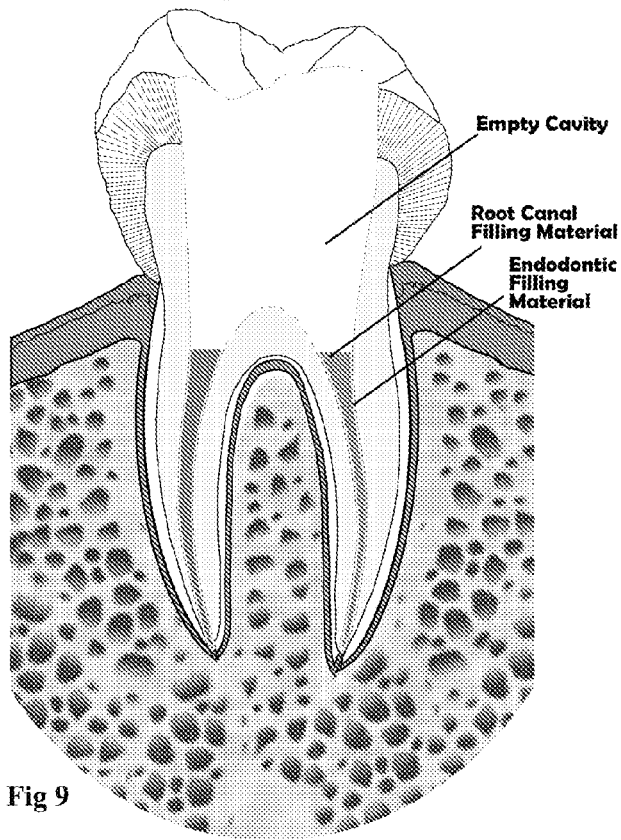
FIG. 9 is a longitudinal view of the tooth of FIG. 8 in which decay has been removed, root canal therapy has been done, and the root canals have been filled with gutta-percha and the endodontic filling material as a root canal sealer.

FIG. 8 shows a longitudinal view of a damaged tooth. The decay has penetrated through the enamel and dentin, reached the pulp, and damaged the entire pulp tissue. Such a tooth needs to be treated with a difficult method as follows: a) the decay has been eliminated and the pulp chamber is exposed, b) using appropriate instruments and root canal procedures the entire damaged or necrotic pulp, microorganisms, and their byproducts is removed, and root canal system has been shaped and cleaned, c) a most common root canal filling material (gutta-percha) is used, d) the inventive endodontic filling material is mixed, transferred, inserted, and it sealed the gap between gutta-percha and root canal walls (FIG. 9).

Figure 10:
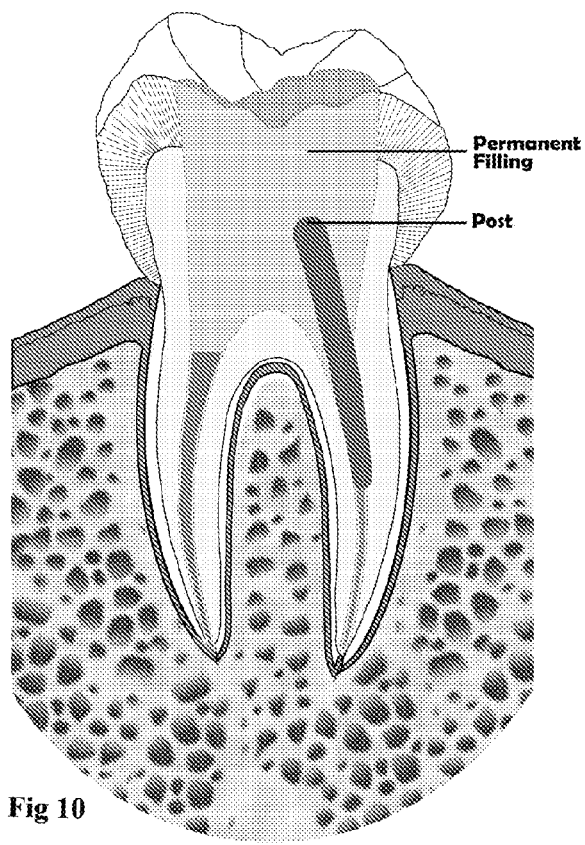
FIG. 10 is a longitudinal view of the tooth of FIG. 9 in which using prefabricated post a permanent filling was done and all the treatments were successful.

FIG. 10 presents a longitudinal view of a tooth in which root canal therapy, post cementation, and permanent coronal filling treatments is succeeded. The supporting periodontal ligament and bone are healthy.

Figure 11:
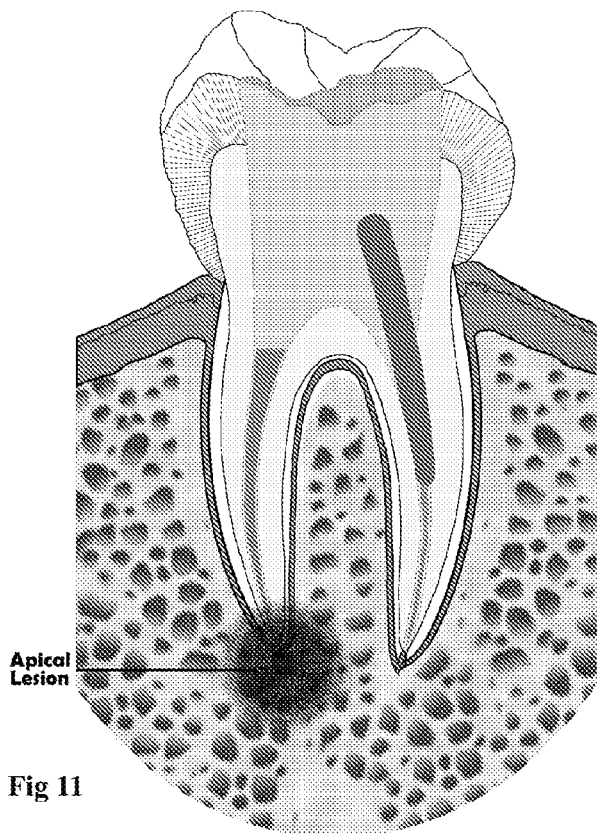
FIG. 11 is a longitudinal view of the tooth of FIG. 10 in which root canal therapy and restorative treatment has been completed, but ReT has failed and a periapical lesion persists.
Figure 12:
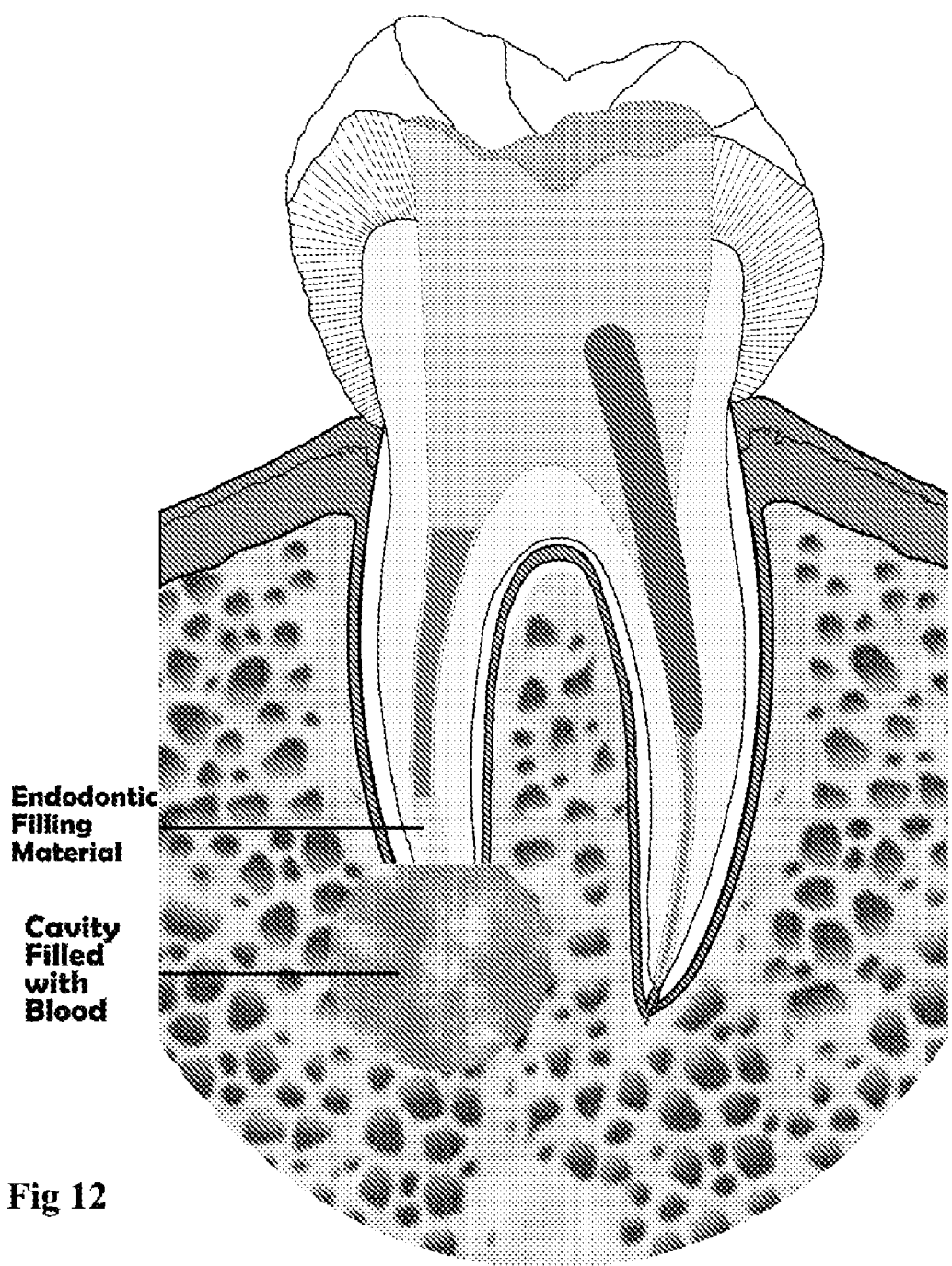
FIG. 12 is a longitudinal view of the tooth of FIG. 11 in which periapical lesion has been removed, periradicular surgery has been completed and root-end filling with the endodontic filling material has been inserted.

In one embodiment, a method of tooth cavity restoration comprises identifying and preparing a site on a tooth which is going to be restored, mixing and applying a composition which consist of: I) a powder, wherein said powder selected from a group consisting of (A) calcium salt compound powder, and (B) calcium oxide compound powder (Aa) calcium silicate compound powder, and (Ab) calcium phosphate compound powder, wherein ratio of (A) to (B)+(Aa)+(Ab), (B) to (A), (Aa) to (A)+(B)+(Ab), or (Ab) to (A)+(B)+(Aa), is between 99 to 111 to 99 percent by weight; II) a liquid, wherein said liquid is selected from a group consisting of: basic, neutralized, acidic water base solution; and III) a mixture, wherein said mixture is prepared by mixing said powder with said water base solution. The preferred site for restoration in an endodontic surgery is a root-end cavity. FIG. 11 depicts a longitudinal view of a tooth in which root canal therapy was failed and a periapical lesion enclosed the infected root apex. Such a tooth needs to be treated with a complicated surgical method as follows: a) incision and reflection of overlaying gingiva, b) osteotomy was done to create an opening window, c) removing the periapical lesion, d) root-end resection and root-end cavity preparation, e) mixing the inventive endodontic filling material, its transferring and insertion by using a suitable carrier, so that it fills and seals the root-end cavity and f) suturing the incision to complete the surgery (FIG. 12). It deserves to be mentioned that after filling the root-end cavity, the bone cavity is filled with blood which is in direct contact with the inventive endodontic filling material.

Figure 13:
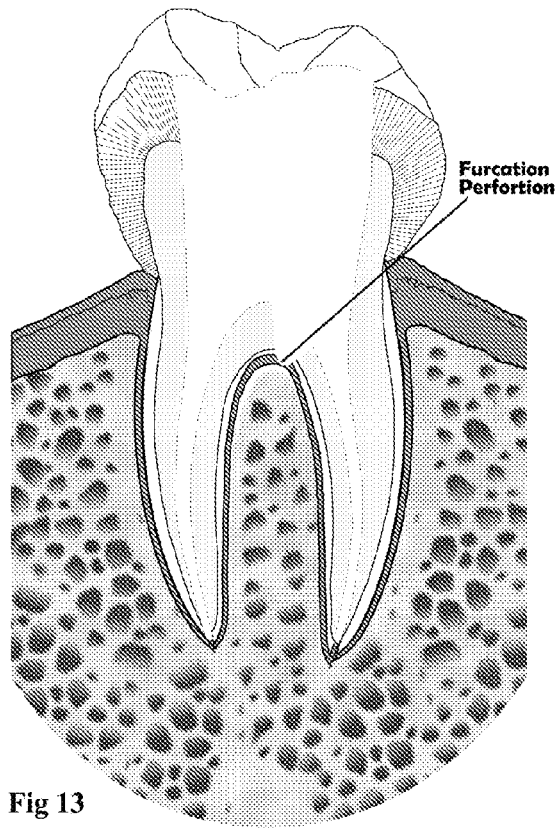
FIG. 13 is a longitudinal view of the tooth of FIG. 1 in which a perforation in the bifurcation has occurred during root canal therapy.
Figure 14:
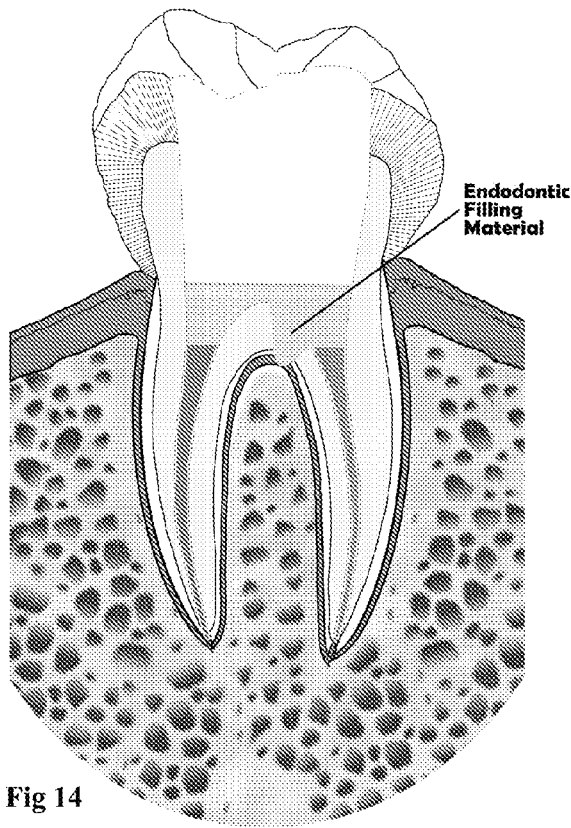
FIG. 14 is a longitudinal view of the tooth of FIG. 13 in which the furcation perforation has been repaired with endodontic filling material after root canal therapy.

FIG. 13 shows a longitudinal view of a tooth in which a perforation in the furcation has been occurred during root canal therapy. As seen in FIG. 14, after root canal therapy the perforation has been repaired with the inventive endodontic filling material.

Another preferred embodiment of the present invention is the method of forming a medical restoration comprising the identification and preparation of a site which is going to be restored and repaired in a portion of a bone; and also mixing and applying a composition which consists of: I) a powder, wherein said powder selected from a group consisting of (A) calcium salt compound powder, and (B) calcium oxide compound powder, (Aa) calcium silicate compound powder, and (Ab) calcium phosphate compound powder, wherein ratio of (A) to (B)+(Aa)+(Ab), (B) to (A), (Aa) to (A)+(B)+(Ab), or (Ab) to (A)+(B)+(Aa), is between 99 to 111 to 99 percent by weight; II) a liquid, wherein said liquid is selected from a group consisting of: basic, neutralized, acidic water base solution; and III) a mixture, wherein said mixture is prepared by mixing said powder with said water base solution.

The following examples give further illustrations of present invention's preferred embodiments, but are not to be construed as in any way limiting the scope of the present invention as set forth in the claims.

Example One

The preferred embodiment of the present endodontic filling material in this example has the following powder and liquid compositions:
A) Powder:
Tricalcium silicate and dicalcium silicate (61%), barium sulfate (14%), tricalcium phosphate and dicalcium phosphate (8%), calcium sulfate (5%), calcium hydroxide (5%), calcium oxide (2%), calcium aluminate (2%), calcium carbonate (2%), and calcium chloride (1%).
B) Liquid:
The liquid was a phosphate buffer saline solution of the following composition: 1.7 g $KH_2PO_4$, 11.8 g $Na_2HPO_4$, 80.0 g NaCl, and 2.0 g KCl in 10 liters of distilled water (pH 7.2).

According to the present invention, the use of the endodontic filling material provided an effective means for pulp capping agents and procedures. In order to determine these capabilities, a study was procedures as follows: a cavity preparation is made in each of the eight animal teeth. During the preparation, exposure of the pulp occurred. Control of bleeding is accomplished with sterile cotton pellet. The endodontic filling material is then mixed on a sterile pad and applied to the exposure site. An appropriate self-curing Fuji II glass ionomer restorative material (GC International Corp, Tokyo, Japan) is applied to fill the prepared cavity and then it was cured.

When the procedure was conducted in this experiment, the results indicated an extremely high level of remaining pulpal vitality (100%) and a complete dentinal bridge formation over the exposed pulp area (75%) after the procedure. No pulpal inflammatory reaction was noted for the treated teeth.

Example Two

The powder and liquid compositions in this example are as follow:
A) Powder:
Tricalcium silicate and dicalcium silicate (48%), tricalcium phosphate and dicalcium phosphate (18%), barium sulfate (15%), calcium hydroxide (6%), calcium sulfate (6%), calcium oxide (3%), calcium carbonate (2%), calcium fluoride (1%), and calcium aluminate (1%).
B) Liquid:
The liquid was a normal saline solution of the following composition: 9.0 g NaCl in 1 liters of distilled water.

The performance of the endodontic filling material with the above composition was evaluated for root-end filling using dye penetration method. This method of measuring the sealing ability of root-end filling materials is well known. In dye penetration test, the root-end cavity is first prepared and then filled with the material to be tested. This test allows a comparison (under controlled conditions) between the sealing ability of standard filling materials, such as MT A, and the cement composition of the present invention. After coating the outside of the tooth with nail varnish in order to prevent dye leakage through anywhere except the cavity which is being tested, the tooth is immersed in dye solution. The tooth is then sectioned and examined under light microscopy, and the degree of dye leakage along cavity walls was measured.

The procedure of such a test was as follows: Sixty-six extracted single rooted of human teeth were cleaned, shaped, and obturated in the same method. Nail varnish was then applied to the entire external surface of each root and was allowed to be dried. Three to four millimeters of the apical segment of each root was removed at a 90 degree angle to the longitudinal axis of the root. The resected surface was acid etched, and a thin layer of pit and fissure sealant was applied to prevent dye penetration through the exposed dentinal tubules. After that, a 3 mm deep root-end cavity was ultrasonically prepared. The samples were randomly divided into 3 test groups, each having 20 roots. Six roots were used as positive and negative control groups. Samples were filled with the described prepared material to be compared with commercially available formulations of IRM (Caulk Dentsply, Milford, Del., USA), and mineral trioxide aggregate (ProRoot MTA, Dentsply Tulsa Dental, Tulsa, Okla., USA). After a day the samples were totally immersed in aqueous solution of methylene blue for 24 hours. Roots were sectioned longitudinally into two halves and the extent of leakage along cavity walls was then observed under the stereomicroscope. The results of the study, expressed in millimeters, are reported. These results in the case of sealing the retrograde cavities, demonstrated the mean microleakage of the endodontic filling material (0.785±0.763 mm) less than IRM (2.675±0.922 mm) and MTA (0.985±0.914 mm), while the statistical difference for these two comparisons was significant and non significant, respectively. Positive and negative controls responded as expected. ANOV A test showed statistically significant differences among experimental groups (P<0.001), but Tukey's test revealed no significant difference between the endodontic filling material of the present invention and MTA as the gold standard. It was concluded that the sealing ability of the endodontic filling material of the present invention and MTA is the same and superior to IRM. Although direct application and relevance of such dye leakage studies to clinical practice has been questioned, such tests are the oldest and easiest method to test new dental materials. Furthermore, when the filling material does not allow penetration of small molecules such as those exhibited in the dye it has a logical potential to prevent leakage of large molecules such as bacteria and/or by-products.

Example Three

The powder and liquid compositions in this example are as follow:
A) Powder:
Tricalcium silicate and dicalcium silicate (40%), tricalcium phosphate (20%), barium sulfate (18%), calcium sulfate (8%), calcium oxide (6%), calcium carbonate (4%), calcium hydroxide (3%), and calcium fluoride (1%).
B) Liquid:
The liquid was a phosphate buffer saline solution of the following composition: 1.7 g KH2P04, 11.8 g Na2HP04, 80.0 g NaCl, and 2.0 g KCl in 10 liters of distilled water (pH 7.2).

Based on the present invention, the use of the endodontic filling material, provided an effective additional seal second seal for the most outer area of the root-end filling material and the surrounding dentin, via its ability of hydroxyapatite crystal formation, so that a hydroxyapatite cap blocked the communication path between root canal system and periradicular area by its adhesion to the material and surrounding dentine the both. The study design for the evaluation of this ability was as follows: Ten extracted single rooted of human teeth were cleaned, shaped, and obturated with gutta-percha in the same method of the second example. Three millimeters of the apical segment of each root was removed. A root-end cavity preparation is made ultrasonically in each tooth. The described prepared material is then mixed and inserted into the root-end cavity. The samples were totally immersed in normal saline solution for 5 months in room temperature. The presence of hydroxyapatite cap was then observed under the scanning electron microscope (SEM).

The results showed that the hydroxyapatite cap was formed over the inventive root-end filling material and surrounding dentine, while the boundary gap between them was sealed by hydroxyapatite crystals. The nature of these crystals was determined by electron probe microanalysis (EPMA) and the results were comparable with standard hydroxyapatite.

Example Four

The compositions of the powder and liquid in this example are as follow:
A) Powder:
Tricalcium silicate and dicalcium silicate (36%), barium sulfate (18%), tricalcium phosphate (12%), calcium sulfate (9%), silica (6%), calcium oxide (6%), calcium hydroxide (6%), calcium carbonate (4%), calcium aluminate (2%), and calcium chloride (1%).
B) Liquid:
The liquid was a salts solution of the following composition: 8.0 g sodium fluoride and 4.0 g calcium hydroxide in 1 liters of distilled water.

Regarding to the present invention, the use of the endodontic filling material provided an antibacterial effect against the invasive microorganisms. It was reported that MTA as a root-end filling material and calcium hydroxide as a successful intracanal dressing material have the reasonable antibacterial property. Using agar diffusion test, the antibacterial effect of the inventive endodontic filling material is evaluated and compared with MT A and calcium hydroxide the both. The design of this study was as follows: a 5 millimeter holes were punched in the sterilized agar. MTA, calcium hydroxide (according to manufacturers' instruction), and the inventive endodontic filling material were then prepared and inserted into the holes. A second layer of agar with a polymicrobial mixture was added and they were stored in the room temperature for 2 hours. The plates were incubated at 37 degree Celsius for 72 hours. The inhibition zones of bacterial growth were measured at 24, 48, and 72 hours.

The results indicated that the mean diameter of inhibition zones detected around the inventive endodontic filling material was remarkably greater than the ones found for MTA and comparable with calcium hydroxide. Using ANOVA test demonstrated that the difference among these three test groups was statistically significant. However, using paired test in order to compare the inventive endodontic filling material with MTA and calcium hydroxide showed significant and non significant differences, respectively.

What it can be implied from various above descriptions and drawings of the present endodontic filling material and the method of its use, is that various features can be used single or in any combination thereof. Therefore, this invention is not necessarily restricted to the preferred embodiments depicted herein. In addition, it should be known that variations and modifications within the field of the invention may occur to those skilled in the art to which the invention pertains. Therefore, the present invention may utilize in other specific forms without departing from its spirit or essential characteristics. Finally, the scope of the invention is indicated by the claims rather than the above description.

What is claimed is:

1. A method of preparation of an antibacterial endodontic filling biomaterial comprising:
   I) preparing a powder by mixing a plurality of calcium compound powders, wherein said plurality of calcium compound powders consist of calcium salt compound powder (A), calcium oxide compound powder (B), calcium silicate compound powder (Aa) and calcium phosphate compound powder (Ab), and wherein an amount of said calcium oxide compound powder (B) is 8-15 percent by weight, and wherein an amount of said calcium silicate compound powder (Aa) is within 47-71 percent by weight, and wherein an amount of said calcium phosphate compound powder (Ab) is within 9-24 percent by weight and ratio of (Ab)/(Aa) is between 13-50 percent;
   II) preparing a liquid, wherein said liquid is selected from a group consisting of: distilled, deionized or salt water base solution with basic, neutralized-or acidic pH; and
   III) preparing a phosphate ($-PO_4$) and calcium ($Ca2+$) enriched mixture for dental/medical use, wherein said mixture is prepared by mixing said powder with said water base solution thereby producing fast setting/antibacterial cement and hydroxyapatite.

2. The method as claimed in claim 1, wherein said calcium salt compound powder is selected from a group comprising of calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof and wherein an amount of said calcium salt compound powder is within 11.6-21 percent by weight.

3. The method as claimed in claim 1, wherein said calcium oxide compound powder is selected from a group comprising of calcium oxide, calcium peroxide, calcium hydroxide, and combinations thereof.

4. The method as claimed in claim 1, wherein said calcium silicate compound powder is selected from a group comprising of tetracalcium silicate, tricalcium silicate, dicalcium silicate, monocalcium silicate, amorphous calcium silicate and combinations thereof.

5. The method as claimed in claim 1, wherein said calcium phosphate compound powder is selected from a group comprising of octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof.

6. The method as claimed in claim 1, wherein a concentration of (A), (B), (Aa), and (Ab) in the powder is within 0.5-92 percent by weight.

7. The method as claimed in claim 1, wherein said liquid includes a water base solution selected from a group comprising of deionize water, distil water, normal saline, phosphate buffer saline solution, and salt solution with basic, neutralize or acidic pH and wherein an amount of said water base solution is in a range of 20 to 40 weight percent.

8. The method as claimed in claim 1, wherein said phosphate ($-PO_4$) and calcium ($Ca2+$) enriched mixture further includes one or more additives selected from a group comprising of a predetermined amount of filler materials, radiopaque materials, antibacterial agents, bioactive and therapeutic materials, antibiotics, gelling agents, medicaments, osteoinductive factors, anti-inflammatory agents, anti-oxidants, polymeric resins, pigments, adhesives, cariostatics, crystal adjustors, viscosity modifiers, preservatives, plasticizers, biomaterials, pore forming agents, resorbable and non-resorbable fibers and meshes, and dyes.

9. The method as claimed in claim 8, wherein said filler material is selected from a group comprising a bioactive glass, bioactive glassceramic, apatite, hydroxyapatite, bioactive calcium phosphate, guttapercha, Portland cement, bone chip, bone crystal, organic or mineral fraction of bone or teeth, fluoride preparation, silica, fumed silica, amorphous silica, silicate glass, glass fiber, quartz, zinc oxide, zirconia, biodegradable polymer, bismuth subcarbonate, lithium silicate, tin oxide, alumina, titania, synthetic peptide containing powder, and combinations thereof.

10. The method as claimed in claim 9, wherein said predetermined amount of filler material in an endodontic filling material is up to 96 percent by weight.

11. The method as claimed in claim 8, wherein the radioopaque material is selected from a group comprising a salt or oxide of silver, barium, strontium, titanium, or bismuth; a metal; glass frits containing heavy metals; a tungsten; an organo-iodine compound, and a combination thereof.

12. The method as claimed in claim 11, wherein concentration of the radiopaque material in the endodontic filling material is present in an amount of up to 24 percent by weight.

13. The method as claimed in claim 1, wherein said calcium salt compound powder, said calcium oxide compound powder, said calcium silicate compound powder and said calcium phosphate compound powder are in the form of a particulate or fibrous in nanosize, microsize, macro size, or mixtures thereof.

14. The method as claimed in claim 1, wherein the endodontic filling material is prepared as a mixture or a paste or a prefabricated kit.

15. The method as claimed in claim 13, wherein said endodontic filling material is nano sized to promote and accelerate a hydroxyapatite formation and a cement hardening.

16. The method as claimed in claim 1, wherein said endodontic filling material or a filling composition has a hardening time of not more than 30-50 minutes.

* * * * *